US012408861B2

(12) United States Patent
Moctezuma de la Barrera et al.

(10) Patent No.: US 12,408,861 B2
(45) Date of Patent: Sep. 9, 2025

(54) SYSTEMS AND METHODS FOR ROBOTIC SOFT TISSUE EVALUATION

(71) Applicant: MAKO Surgical Corp., Fort Lauderdale, FL (US)

(72) Inventors: Jose Luis Moctezuma de la Barrera, Freiburg (DE); Hyosig Kang, Weston, FL (US); Matt Harrow, Fort Lauderdale, FL (US)

(73) Assignee: MAKO Surgical Corp., Weston, FL (US)

( * ) Notice: Subject to any disclaimer, the term of this patent is extended or adjusted under 35 U.S.C. 154(b) by 635 days.

(21) Appl. No.: 16/817,064

(22) Filed: Mar. 12, 2020

(65) Prior Publication Data

US 2020/0289050 A1  Sep. 17, 2020

Related U.S. Application Data

(60) Provisional application No. 62/817,355, filed on Mar. 12, 2019.

(51) Int. Cl.
*A61B 5/00* (2006.01)
*A61B 5/11* (2006.01)
(Continued)

(52) U.S. Cl.
CPC .......... *A61B 5/4533* (2013.01); *A61B 5/1121* (2013.01); *A61B 5/4585* (2013.01);
(Continued)

(58) Field of Classification Search
CPC ................. A61B 5/1114; A61B 5/1121; A61B 5/1122; A61B 5/4528; A61B 5/4533;
(Continued)

(56) References Cited

U.S. PATENT DOCUMENTS 10,198,968 B2   2/2019  Imhauser et al.
2006/0142657 A1* 6/2006  Quaid .................... A61B 90/37
                                                 600/424
(Continued)

FOREIGN PATENT DOCUMENTS

CN      101711127 A     5/2010
CN      107995855 A     5/2018
(Continued)

OTHER PUBLICATIONS

International Search Report and Written Opinion for International Application No. PCT/US2020/022386, mailed Jul. 3, 2020, 18 pages.

*Primary Examiner* — Jennifer Robertson
*Assistant Examiner* — Nidhi N Patel
(74) *Attorney, Agent, or Firm* — FOLEY & LARDNER LLP

(57) ABSTRACT

A method of robotically evaluating soft tissue characteristics of a joint includes measuring, by a robotic device, information about a joint during a controlled range of motion manipulation of the joint; determining a motion limit of the joint, using the information about the joint measured during the controlled range of motion manipulation of the joint, wherein the motion limit is at least one of a displacement limit or a force limit of the joint; and replicating, using a joint positioner controlled by the robotic device, the controlled range of motion manipulation of the joint while introducing perturbations to the joint, wherein the replicated range of motion manipulation is controlled, at least in part, based on the motion limit. The method further includes using data obtained by the computer-assisted surgery system during the range of motion manipulation with perturbations to characterize the constraints of a soft tissue envelope of the joint.

19 Claims, 9 Drawing Sheets

(51) Int. Cl.
*A61B 34/10* (2016.01)
*A61B 34/20* (2016.01)

(52) U.S. Cl.
CPC .............. *A61B 34/10* (2016.02); *A61B 34/20* (2016.02); *A61B 2034/102* (2016.02); *A61B 2034/105* (2016.02); *A61B 2034/2055* (2016.02); *A61B 2034/2059* (2016.02); *A61B 2034/2063* (2016.02); *A61B 2562/0252* (2013.01)

(58) Field of Classification Search
CPC ..... A61B 5/4585; A61B 5/702; A61B 5/7275; A61B 34/10; A61B 34/20; A61B 2034/102; A61B 2034/105; A61B 2034/2055; A61B 2034/5059; A61B 2034/2063; A61B 2562/0252; A61B 2505/05
See application file for complete search history.

(56) References Cited

U.S. PATENT DOCUMENTS

| | | |
|---|---|---|
| 2007/0055176 A1 | 3/2007 | Branch et al. |
| 2009/0209884 A1 | 8/2009 | Van Vorhis et al. |
| 2014/0081181 A1 | 3/2014 | Branch et al. |
| 2014/0188129 A1 | 7/2014 | Kang |
| 2016/0278754 A1 | 9/2016 | Todorov et al. |
| 2017/0360512 A1 | 12/2017 | Couture et al. |
| 2018/0132949 A1 | 5/2018 | Merette et al. |

FOREIGN PATENT DOCUMENTS

| | | |
|---|---|---|
| CN | 109009176 A | 12/2018 |
| EP | 3 251 589 A1 | 12/2017 |
| JP | 2018-050928 A | 4/2018 |
| WO | WO-2016/148257 A1 | 9/2016 |

\* cited by examiner

SYSTEMS AND METHODS FOR ROBOTIC SOFT TISSUE EVALUATION

CROSS-REFERENCE TO RELATED APPLICATIONS

This application claims the benefit of and priority to U.S. Provisional Patent Application No. 62/817,355, filed Mar. 12, 2019, which is incorporated by reference herein in its entirety.

BACKGROUND

The present invention relates generally to the field of surgical robotic devices and more particularly to the field of surgical robotic devices configured to assist with the evaluation of knee ligament tension in a partial or total knee replacement procedure.

Some patients who undergo a partial or total joint replacement surgery later have complications relating to the joint replacement surgery. These complications can cause patient discomfort, can create limitations with the joint's range of motion or balance, and may even necessitate a revision surgery. Soft tissue balancing helps ensure that the result of the partial or total joint replacement surgery is a balanced joint, which increases the replacement joint's performance, decreases patient discomfort, and lessens the likelihood of subsequent complications. For example, with a partial or total knee replacement surgery, ligament balancing (e.g., created by dissecting or tightening the ligaments of the knee) may result in a balanced knee. Additionally, pre-operative planning of the joint replacement prosthetic(s) may help assure that the result of the surgery is a balanced joint.

Traditionally, surgeons have manually evaluated the soft tissue of a joint undergoing a partial or total joint replacement surgery in order to achieve a balanced joint. For example, a surgeon may implant a trial implant in a knee joint and manually test the knee joint in flexion and extension to determine which ligaments to cut and by how much to reduce joint tightness.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

The computer-assisted surgery system and the robotic ligament evaluator system described herein can be used in any context to position and evaluate a joint. For example, a surgeon may use the robotic ligament evaluator system during a total or partial knee replacement surgery to intraoperatively assess and make adjustments to the knee ligaments. However, embodiments of the present disclosure are not limited to the evaluation of the knee or to the evaluation of ligaments. Accordingly, the robotic ligament evaluator system described herein may also be used to position and evaluate the soft tissues of various other joints including, but not limited to, a hip, an ankle, an elbow, a shoulder, or a wrist.

In addition, the computer-assisted surgery system and the robotic ligament evaluator system described herein may be used at any stage in the medical treatment of a patient. For example, a surgeon may use the robotic ligament evaluator system prior to performing a surgical procedure. As another example, a surgeon may use the robotic ligament evaluator system during a surgical procedure. As a third example, a surgeon may use the system during pre- or post-operative examinations in order to assess the condition of the joint and gauge the success of the surgery. In a fourth example, the system may be used while imaging the joint.

Various features of a robotic assisted ligament evaluator system and methods according to the present disclosure will now be described in greater detail.

Exemplary Robotic Ligament Evaluator System

Figure 1:
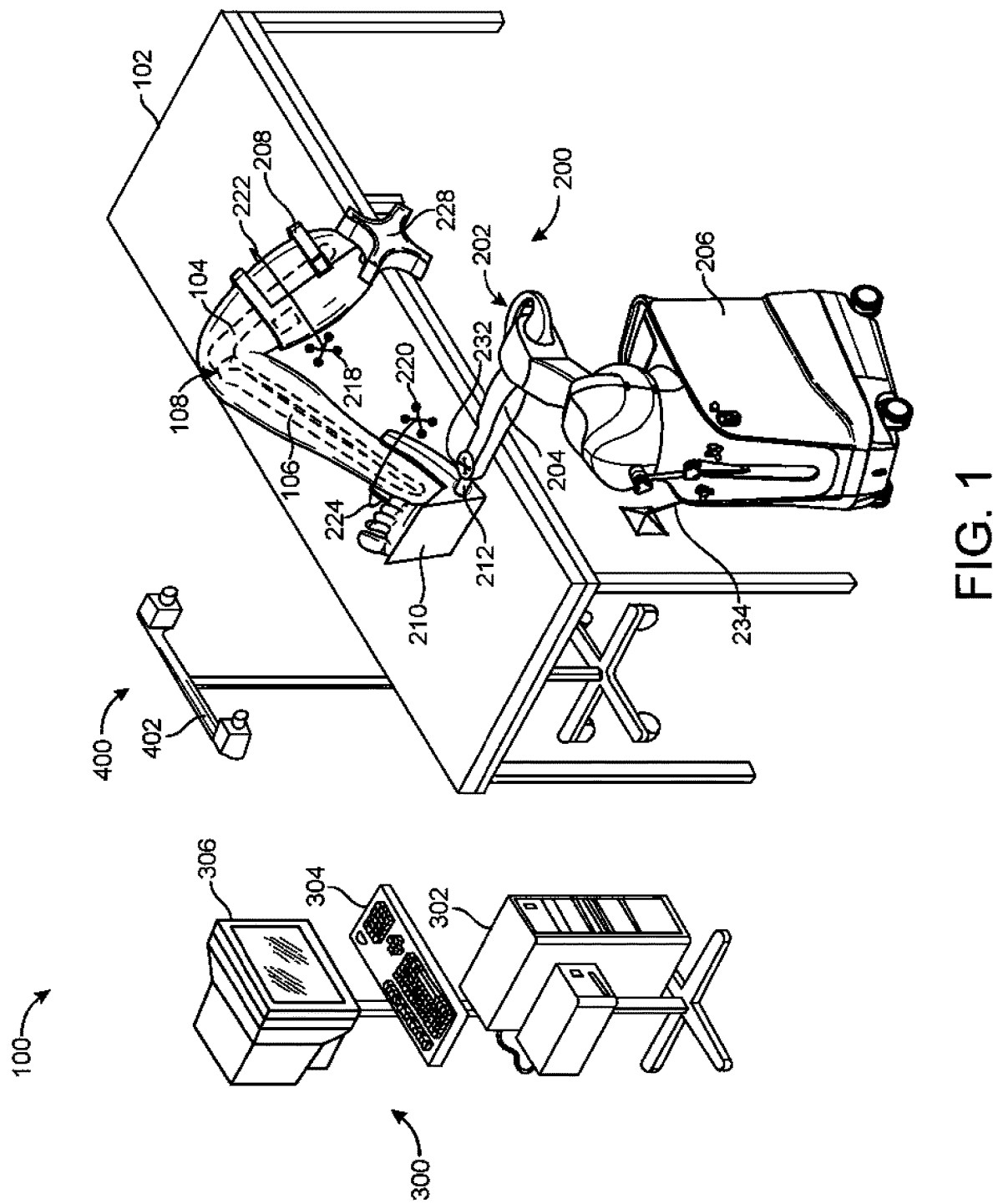
FIG. 1 is a computer-assisted surgery system that includes a robotic ligament evaluator, according to an exemplary embodiment.

Referring to FIGS. 1-4, a robotic ligament evaluator system 200 according to an exemplary embodiment includes a robotic device 202 and a joint positioner comprising a proximal brace and a distal brace. In this exemplary embodiment, the robotic ligament evaluator system 200 is configured to be used on a knee joint 108, formed by a femur 104 and a tibia 106 of a patient. Accordingly, the proximal brace is shown in FIG. 1 as a thigh brace 208, and the distal brace is shown as a foot brace 210. The thigh brace 208 and the foot brace 210 can be any suitable structures for grasping, holding, supporting, or otherwise associating with a portion of a patient. In the embodiment shown in FIGS. 1-4, the braces 208 and 210 are cuffs. The patient's upper leg (i.e., anatomy including and surrounding the femur 104) rests in the thigh brace 208, and the patient's lower leg (i.e., anatomy including and surrounding the tibia 106) rests in foot brace 210. The braces 208 and 210 may further include one or more straps, buckles, coverings, etc. for securing the patient to the braces 208 and 210.

In various embodiments, the robotic device 202 has force-torque sensing capabilities and includes a robotic arm 204 coupled to a base 206. The robotic arm 204 is driven by actuators, such as encoders. Additionally, robotic arm 204 includes an interface tool 212 configured to couple the robotic arm 204 to the foot brace 210 (e.g., by a robotic arm interface 230, shown in FIG. 2). The thigh brace 208 is coupled to a securing mechanism, shown as a clamp 228. The clamp 228 is configured to removably couple to a surface. In FIGS. 1-4, the clamp 228 is shown coupled to an operating table 102. In this way, the clamp 228 affixes the thigh brace 208 in place and causes the thigh brace 208 to be stationary during a medical procedure. As such, the proximal femur is a stationary bone during the ligament evaluation process described herein, and the distal tibia is a mobile bone. In other embodiments, the femur is not stationary and is allowed to rotate about the hip joint. In such embodiments, the thigh brace 208 is also robotically controlled and may function in a stationary, freely moving, or robotically positioned mode, as needed.

As described above, the robotic arm 204 can include one or more encoders. The encoders of the robotic arm 204 may be any commercially available encoders and may be rotational or linear actuators. The encoders are configured to enable force-control and high-precision position control of the robotic arm 204. Multiple encoders can be linked to provide position control in numerous degrees of freedom. For example, the robotic arm 204 may include two joints for two degrees of freedom (DOF) or six joints for six DOF. Each joint can be controlled by a corresponding encoder, and as many joints (and corresponding encoders to control the joints) as desired may be linked to form robotic arms with the DOF. Rotational or linear encoders may be chosen to obtain a compact design of the robotic arm 204.

Referring specifically to FIG. 1, the robotic ligament evaluator system 200 may be used in connection with a computer-assisted surgery (CAS) system 100. The CAS system 100 may include, among other components, the robotic ligament evaluator system 200 including the robotic device 202, a computer system (represented in the figures as a computer system 300, including a processing circuit/computer 302, an input device 304, and a display 306), and a secondary tracking system 400. The robotic device 202 is an interactive device used by a surgeon during a surgical procedure, such as the robotic device described in U.S. Pat. No. 8,010,180, titled "Haptic Guidance System and Method," which is hereby incorporated by reference herein in its entirety.

The robotic ligament evaluator system 200 can be controlled (e.g., by computer system 300 or manually by a user) to position the patient's joint. For example, the patient's knee may be brought from a flexed position to a fully extended position. The computer system 300 may control the robotic ligament evaluator system 200 coupled to the foot brace 210 (and thus the portion of the patient held by the brace 210) to move to and/or maintain a desired position in order to gather data about the knee joint 108. The computer system 300 can control the robotic ligament evaluator system 200 before, during, or after a surgical procedure to evaluate the soft tissue balance of the knee joint. Additionally, during the surgical procedure, the computer system 300 can control the robotic ligament evaluator system 200 to bring the foot brace 210 to positions corresponding to different stages of a surgical plan. For example, if a certain stage of a knee replacement surgery requires the femur 104 and tibia 106 to be pulled away from each other, the computer system 300 can be programmed to control the motorized robotic ligament evaluator system 200 to accomplish this positioning.

The force control capabilities of the encoders enable the robotic ligament evaluator system 200 to fully compensate for the weight of the patient's extremity or other body part held by the system 200. In one embodiment, the robotic ligament evaluator system 200 applies forces to the thigh brace 208 and the foot brace 210 to counteract the weight of the portion of the patient's anatomy held by the robotic ligament evaluator system 200 (e.g., the patient's leg). This gravity compensation feature causes the portion to feel weightless as a user is manually repositioning the evaluator system 200 (e.g., moving the brace 210 with the portion of the anatomy held therein). Consequently, the user is able to manually reposition the evaluator system 200 without having to exert additional effort to lift or move the weight of the portion of the patient's anatomy. The backdrivability of the encoders further contribute to the ease with which a user can manually adjust the evaluator system 200 (i.e., manually adjust the position of the thigh brace 208 and the foot brace 210).

In one embodiment, the robotic ligament evaluator system 200 may operate in three modes. In a first mode, the evaluator system 200 operates to hold the joint in a fixed position. This first mode may be useful, for example, while a surgeon is using the robotic device 202 to sculpt or otherwise modify the patient's joint. For example, in one embodiment, the CAS system 100 may be programmed to hold the evaluator system 200 in a fixed position while a second surgical device (not shown) is in a cutting mode and configured to operate on the joint. In a second mode and a third mode, the evaluator system 200 operates to reposition the joint. These modes may be useful during surgical planning, when moving from one step of a surgical procedure to another, or when performing a soft tissue balancing (e.g., a ligament evaluation) procedure. In the second mode, the evaluator system 200 may reposition the joint (e.g., "active" mode). In the third mode, the evaluator system 200 may allow the user to reposition the joint and aid the user in repositioning the joint (e.g., "passive" mode). For example, the encoders within the robotic arm 204 provide a backdrivable system, allowing the user to manually manipulate the positions of the thigh brace 208 and the foot brace 210. The CAS system 100 determines how much force is required to compensate for the weight of the patient's leg and can sense incremental changes in force as a user manipulates the position of the evaluator system 200 and the knee joint 108.

As described above, the robotic arm 204 couples to the foot brace 210 via the interface tool 212 (e.g., which couples to the robotic arm interface 230 of the foot brace 210). In various embodiments, the interface tool 212 may be one of many interchangeable surgical tools adapted to work with the robotic arm 204. Other tool examples may include burrs, drills, probes, saws, microscopes, laser range finders, cameras, lights, endoscopes, ultrasound probes, irrigation devices, suction devices, and radiotherapy devices. The interface tool 212 may be secured to the robotic arm with conventional hardware, such as screws, pins, or clamps, a keyed connection, detents, threaded connectors, an interference fit, or any other method that permits interface tool 212 to be removably engaged with the robotic arm 204.

The processing circuit of the CAS system 100 is utilized to implement the various functions (e.g., calculations, control mechanisms, processes) described herein, such as computerized control of the robotic ligament evaluator system 200. The processing circuit includes a processor and memory (e.g., provided in the computer 302). The processor can be implemented as a general purpose processor, an application specific integrated circuit (ASIC), one or more field programmable gate arrays (FPGAs), a group of processing components, or other suitable electronic processing components. The memory (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory may be or include volatile memory or non-volatile memory. Further, the memory may be a non-transient memory. The memory may include database components, object code components, script components, or any other type of information structure for supporting the various activities and information structures described in the present application. According to an exemplary embodiment, the memory device is communicably connected to the processor and includes computer code for executing one or more processes described herein.

The robotic ligament evaluator system 200 may communicate with the computing system 300 via a communications interface. The communications interface can be or include wired or wireless interfaces for conducting data communications with external sources via a direct connection or a network connection (e.g., an Internet connection, a LAN, WAN, or WLAN connection). For example, in some embodiments, the communications interface includes an Ethernet card and port for sending and receiving data via an Ethernet network. In other embodiments, the communications interface includes a WiFi transceiver for communication over a wireless network. Additionally, a user may communicate with the robotic ligament evaluator system 200 using the input device 304 and/or the display 306. For example, the display 306 may display commands for the evaluator system 200 that the user selects using the input device 304. The display may further allow the evaluator system 200 to communicate with the user, for example, by displaying data or other information gathered by the evaluator system 200.

Figure 2:
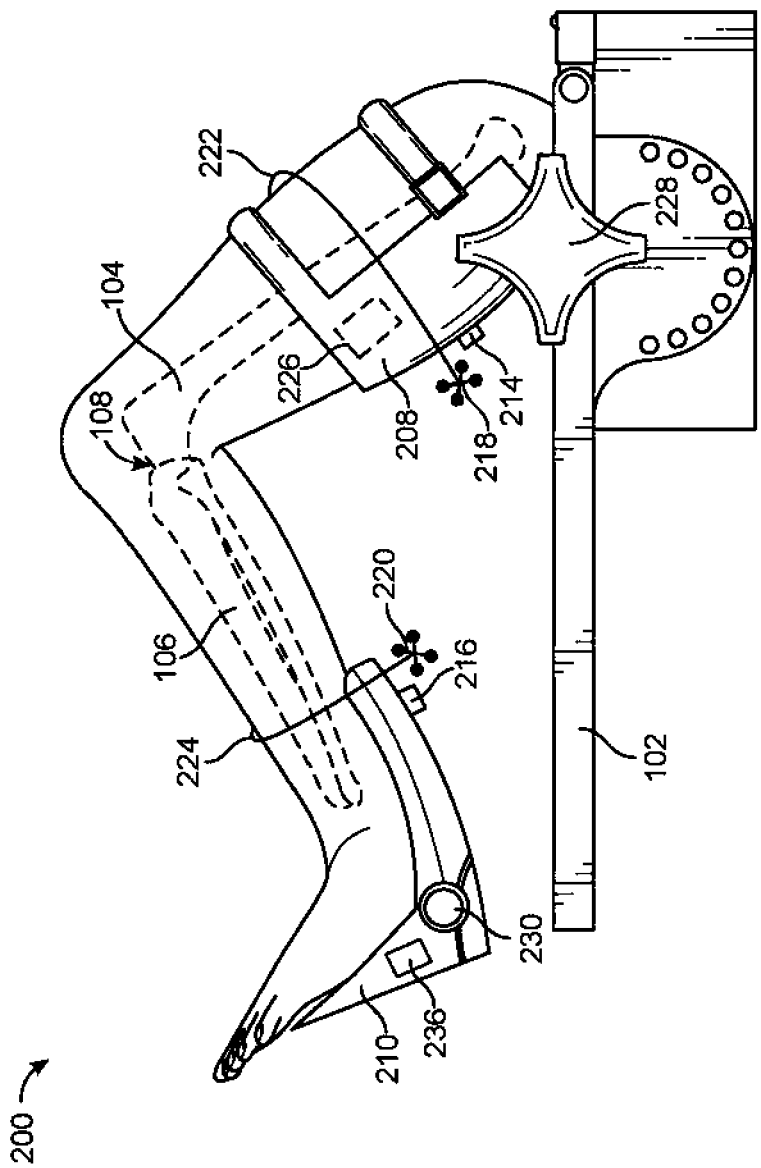
FIG. 2 is a side view of the robotic ligament evaluator of FIG. 1, according to an exemplary embodiment.

In one embodiment, the robotic ligament evaluator system 200 includes a local tracking system to track a portion of a patient's anatomy (e.g., the portions held by the evaluator system 200) relative to the evaluator system 200. The tracking system can be any commonly known tracking method such as magnetic, imaging (x-ray, CT, MRI, ultrasound), video, fiber optic, optical or mechanical. In FIG. 2, the tracking system is an optical tracking system that includes a thigh detection device 214 and a foot detection device 216. The detection devices 214 and 216 are fixed to the thigh brace 208 and foot brace 210, respectively. Additionally, in FIG. 2, the tracking system further includes a thigh trackable marker 218 and a foot trackable marker 220, which are fixed to the portion of the patient's anatomy held by the evaluator system 200 (i.e., the patient's femur 104 and tibia 106) and are detectable by the thigh detection device 214 and the foot detection device 216. In one embodiment, the detection devices 214 and 216 include a visible light-based detector, such as a MicronTracker (Claron Technology Inc., Toronto, Canada), that detects a pattern (e.g., a checkerboard pattern) on the trackable markers 218 and 220. As is known, the trackable markers 218 and 220 may be active (e.g., light emitting diodes, or LEDs) or passive (e.g., reflective spheres, a checkerboard pattern, etc.), and may have a unique geometry (e.g., a unique geometric arrangement of the markers) or, in the case of active wired markers, a unique firing pattern.

The trackable markers 218 and 220 are affixed to the tracked objects (e.g., the patient's bones femur 104 and tibia 106, respectively) in a secure and stable manner. In the embodiment of FIGS. 1-4, the trackable markers 218 and 220 are fixed to the patient's bones (i.e., the patient's femur 104 and tibia 106, respectively) with a femur bone pin 222 and a tibia bone pin 224, respectively. Additional trackers could be attached to, for example, the thigh brace 208, clamp 228, and/or foot brace 210. In operation, the detection devices 214 and 216 detect positions of the trackable markers 218 and 220. The pose of the tracked objects (e.g., the patient's femur 104 and tibia 106) relative to the detection device(s) 214 and 216 can then be calculated based on the trackable elements' positions, unique geometry, and known geometric relationship to the tracked objects. In this manner, the pose of the tracked objects can be calculated relative to the robotic ligament evaluator system 200.

In another embodiment, the distal brace (e.g., the foot brace 210) includes a three-dimensional (3D) tracking sensor 236, such as the 3D tracking sensor developed by Leap Motion, Inc. (San Francisco, CA). The three-dimensional tracking sensor 236 is able to track the pose of the trackable markers 218 and 220, as described in U.S. Pat. No. 9,192,445, titled "Registration and Navigation Using a Three-Dimensional Tracking Sensor," issued Nov. 24, 2015, which is hereby incorporated by reference herein in its entirety.

Inclusion of a local tracking system, as shown in FIG. 2, may provide advantages over use of a non-local (i.e., global) tracking system to track the portion of the patient's anatomy. Some types of global tracking systems utilize a detection device fixed relative to an operating room. The operating room may contain various tracked objects, such as the patient's bones and surgical tools. If the global tracking system is an optical tracking system, a line of sight from the trackable elements and the detection device may be required. If objects or people block the path from the trackable elements to the detection device, an interference in the tracking process may result. Use of a local tracking system, as shown in FIG. 2, minimizes line-of-sight issues by placing the detection devices 214 and 216 in close proximity to the trackable elements 218 and 220. In this manner, the local tracking system can continuously track the position of the patient's bones, which may be coupled to the trackable elements 218 and 220 via bone pins 222 and 224.

In one embodiment, shown in FIG. 1, the CAS system 100 includes both a local tracking system and the secondary, global tracking system 400. The secondary tracking system 400 can be used to track additional objects in the CAS system 100, and may include a secondary detection device 402 and additional trackable markers. The additionally trackable markers may include a robotic arm trackable marker 232 located on the robotic arm 204 and a robotic device trackable marker 234 located on the base 206 of robotic device 202.

The local tracking system may be in communication with the global tracking system 400 such that the position of all tracked objects in the CAS system 100 can be calculated with respect to a single coordinate frame of reference (i.e., a "global reference system" or a "global coordinate system"). In one embodiment, an additional trackable marker is placed on a stationary portion of the robotic ligament evaluator system 200 (e.g., on the clamp 228, on the thigh brace 208). This additional trackable marker is tracked by the secondary tracking system 400. The CAS system 100 can then use the pose of the additional trackable marker to correlate the coordinate systems of the local tracking system and the secondary tracking system 400. In another embodiment, a mechanical tracking system is coupled to the evaluator system 200 (e.g., to the detection devices 216 and 218 or to another portion of the evaluator system 200). The mechanical tracking system is used to track the evaluator system 200. The CAS system 100 can then use information from the mechanical tracking system to correlate the coordinate systems of the local tracking system and the secondary tracking system 400.

Alternatively, or additionally, the secondary tracking system 400 and the local tracking system may operate independently. In one embodiment, the secondary tracking system 400 is configured to independently track the position of portion of the patient's anatomy held by the braces 208 and 210 and register the position of the portion of the anatomy to the global coordinate system. In some cases, tracking the patient anatomy for understanding range of motion and other joint kinematics can be performed outside of the operating room. For example, trackers may be attached directly to the patient (for example, on the skin) or on the patient's clothing. In such cases, the tracking may take place in a physician's office or in connection with physical therapy, for example. For example, the secondary tracking system 400 may track the positions of the trackable markers 218 and 220 attached to the patent through the bone pins 222 and 224. Then, using a predefined relationship between the trackable markers 218 and 220 and the patient's anatomy, the secondary tracking system 400 may register the position of the patient's anatomy on the global coordinate system using the tracked positions of the trackable markers 218 and 220.

In one embodiment, the robotic ligament evaluation system 200 includes features useful for registration of the patient's anatomy (e.g., the portion of the patient's anatomy held by the proximal brace and the distal brace) to a three-dimensional representation of the portion of the patient's anatomy. The portion of the patient's anatomy is registered to allow the local tracking system (or the secondary tracking system 400) to accurately monitor the position of the portion of the patient's anatomy during a medical procedure. The three-dimensional representation may be obtained by any known imaging techniques (e.g, CT or MRI). Alternatively, the three-dimensional representation may be obtained using an imageless system. Imageless systems include technologies that are known in the art, such as systems utilizing statistically shaped models and methods of bone morphing.

In one embodiment, the evaluation system 200 includes an XY array of ultrasound transducers 226, as shown in FIG. 2 and as described in U.S. patent application Ser. No. 13/710,955, titled "Registration Using Phased Array Ultrasound," filed Dec. 11, 2012, which is hereby incorporated by reference herein in its entirety. The ultrasound transducers 226 are used to register the patient's anatomy to the three-dimensional representation. The ultrasound transducers 226 may be located on the interior of one or both braces 208 and 210, such that the transducers 226 are able to scan the patient's bone structure and/or soft tissue. Further, the ultrasound transducers 226 are communicably coupled to the processing circuit (i.e., the computer system 300) for controlling the operation of the transducers 226 and for registering the portion of the patient's anatomy to a three-dimensional representation of the portion of the patient's anatomy. In one method of registration using the robotic ligament evaluator system 200, the locations of the thigh brace 208 and the foot brace 210 are known. The locations of the braces 208 and 210 are known either by fixing a portion of brace (e.g., to the operating table 102, as with the clamp 228) or by tracking the evaluator system 200 with a tracking system (e.g., with the secondary tracking system 400). If the ultrasound transducers 226 are fixed to the braces 208 and 210, the location of the transducers 226 can also be determined. The transducers 226 are controlled to create an acoustic wave directed towards a portion of the patient's anatomy suitable for registration (e.g., a portion of bone or soft tissue having features that can be aligned with the three-dimensional representation of the bone). Because the location of the transducers 226 are known, the location of bone (e.g., femur 104, tibia 106) scanned by the transducers 226 can be calculated. This information can be used to register the portion of the patient's anatomy to the three-dimensional representation.

Including an array of ultrasound transducers in the robotic ligament evaluator system 200 advantageously allows for continuous registration of a portion of a patient's anatomy during a surgical procedure. In contrast, certain other methods of registration are typically performed prior to a surgical procedure or intermittently during a surgical procedure. These other methods may require the surgeon to perform steps such as using a probe to physically contact the patient's bone. Furthermore, interruptions in tracking of the patient can cause errors in registration, requiring the surgeon to stop the procedure in order to reregister the patient. Interruptions in tracking may be caused by an occlusion of a trackable marker or a sudden movement of a tracked object. In the CAS system 100 shown in FIG. 1, the transducers 226 of the evaluator system 200 can be utilized to continuously scan a portion of the patient's anatomy. Using information obtained by the transducers 226, the processing circuit can continuously register the portion of the patient's anatomy. This continuous registration prevents the surgeon from having to stop a surgical procedure to reregister the patient after an interruption of a global tracking system has caused a registration error.

In one embodiment, the processing circuit may create or obtain a three-dimensional representation of the patient's joint prior to a surgical procedure and a three-dimensional representation of the patient's joint during or after the surgical procedure. Additionally, the processing circuit may register the patient's anatomy to either or both three-dimensional representations. The CAS system 100 may then use the three-dimensional representations during surgical planning, such as in determining the joint's soft tissue balance or in determining a position for an implant, and/or in surgical evaluation, such as in determining whether the post-surgery joint is properly balanced.

It is noted that bone registration does not need to be completed prior to the initial range of motion evaluation which is described in more detail below. For this stage of the process, trackers can be attached to the bones and motion recorded without prior registration. Registration is needed during the surgical planning and prior to cutting. It may be possible to have range of motion measurements with pinless tracking. Furthermore, motion can be recorded prior to the main surgical incision in order to best evaluate the uncut soft tissue strength.

Exemplary Soft Tissue Balancing Processes

As described above, the robotic ligament evaluator system 200 may operate in several modes, with some of the modes being limb repositioning modes. These modes may be useful in evaluating the soft tissue balance of the joint of interest. For example, in many surgical knee replacement procedures, the ligaments of the knee are assessed in order to achieve a proper post-operation ligament balance. This is important because a proper ligament balance provides a better limb alignment, prevents asymmetrical wear of implants, provides a lower rate of prosthetic loosening, decreases patient pain, and lessens the likelihood of subsequent complications. Traditionally, ligament balancing has been accomplished by a surgeon manually manipulating the limb to determine which ligaments to dissect and, less frequently, to tighten in order to provide the proper knee balance.

FIGS. 5-16 illustrate various processes that are part of performing a ligament tension evaluation using the CAS system 100. In describing the processes, reference is made to the CAS system 100 and ligament evaluation system 200 as shown in FIGS. 1-4 and to the knee joint 108. However, those of skill in the art will appreciate that the processes of FIGS. 5-16 may be applied to other joints, such as the hip joint, the ankle joint, the elbow joint, the shoulder joint, or the wrist joint. Additionally, some or all of the processes may be performed pre-surgery, during surgery, and post-surgery.

In various embodiments, as described in further detail below, an initial range of motion for the patient is determined by exercising the articulation of the limb through its range of motion without applying stresses. The robotic ligament evaluator system 200 uses information from the determined initial range of motion to move the patient's joint (e.g., the knee joint 108) prior to surgery, during surgery, and/or post-surgery to obtain one or more data sets representative of the patient's soft tissue balance. During the preoperative initial range of motion evaluation, allowable loads and displacements for a joint are determined.

For the initial range of motion evaluation, the joint is exercised through its range of motion without applying stresses. The range of motion could be created by the patient, or a surgeon (or other medical provider) could create the range of motion. The range of motion may be completed manually, and may be done with the anatomy free from the thigh brace 208 and foot brace 210, or by using the robotic device 202 in a passive mode, as described above. The CAS system 100 then tracks and records the range of motion using a tracking system, such as tracking system 200 or 400, tracking the trackable markers 218 and 220, or by one or more video cameras in connection with image recognition software. In one embodiment, the CAS system 100 may record the range of motion as discrete points defining the spatial trajectory that the surgeon performs while exercising the joint through its range of motions. In this way, the CAS system 100 may determine the natural range of motion of the joint and record the natural range of motion as the initial range of motion ("initial ROM"). The initial ROM then serves as a reference range of motion for later stages of the ligament tension evaluation procedure. Locations of the bones through the range of motion can provide measurements directed to, for example, the angle of motion of the bones or the directions of pulling by the ligaments.

Figure 4:
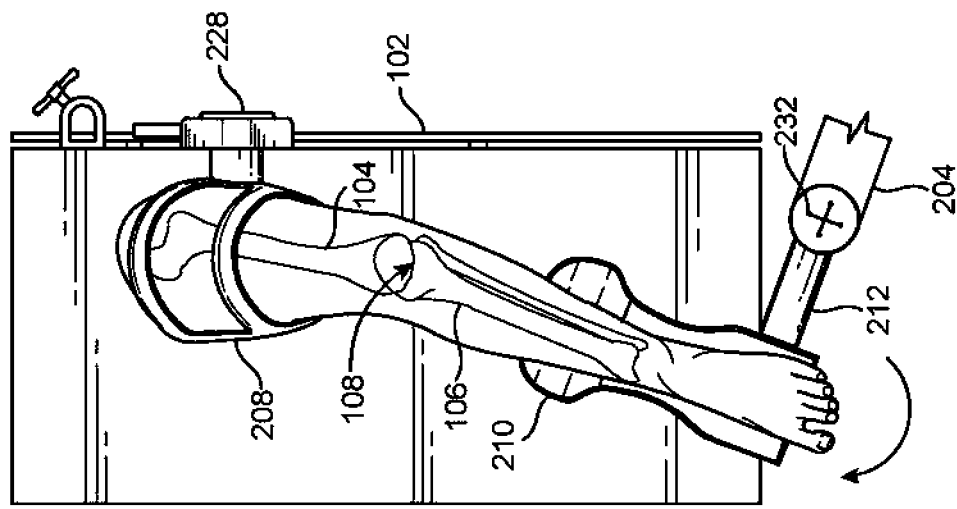
FIG. 4 is top view of a ligament evaluation performed by the robotic ligament evaluator of FIG. 1, according to an exemplary embodiment.
Figure 3:
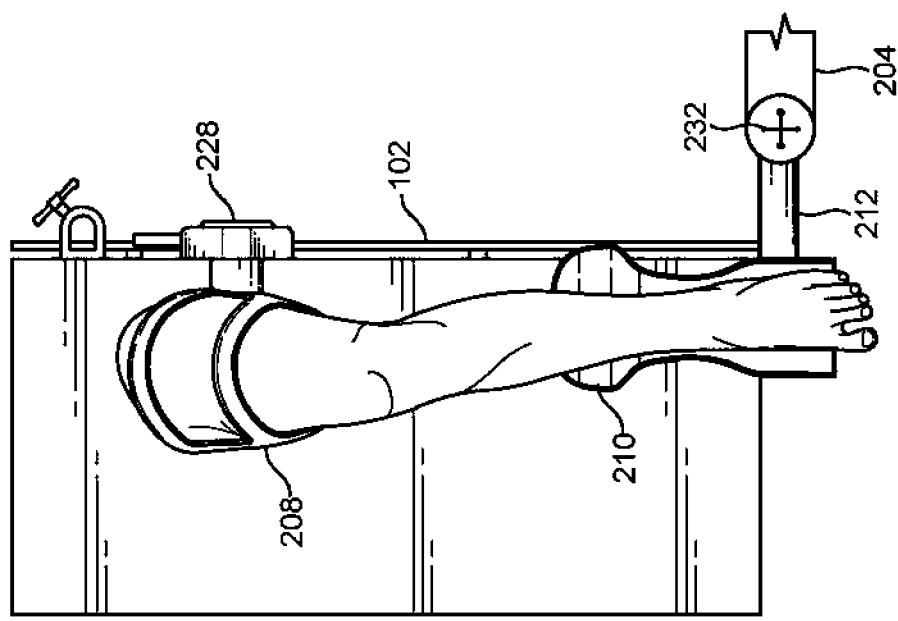
FIG. 3 is top view of the robotic ligament evaluator of FIG. 1, according to an exemplary embodiment.

This process may be illustrated with reference to the knee. For example, the surgeon may take the knee joint 108 through flexion and extension ranges of motion, medial and lateral ranges of motion (as depicted in FIG. 4), torque ranges of motion, and so on. The CAS system 100 determines the range of motion of the knee joint 108 by tracking the relative position of the bones of the knee joint 108 (i.e., the femur 104 and the tibia 106) as the surgeon exercises the knee joint 108 through its range of motion. In one embodiment, the thigh brace 208 and the foot brace 210 are not coupled to the patient while the surgeon exercises the knee joint 108 through its range of motion. The CAS system 100 thus tracks the range of motion through the secondary tracking system 400 tracking trackable markers. In another embodiment, the thigh brace 208 and the foot brace 210 are coupled to the patient, and the robotic ligament evaluator system 200 operates in a passive mode while the surgeon exercises the knee joint through its range of motion. The CAS system 100 then tracks the range of motion through the local tracking system (e.g., by the thigh detection device 214, the foot detection device 216, and/or the three-dimensional tracking sensor 236) and/or through the secondary tracking system 400. The CAS system 100 records the tracked positions of the femur 104 and the tibia 106 as the initial ROM of the knee joint 108.

The preoperative set of data from the initial ROM may include, for example, the distance of the gap in the patient's knee when the knee joint 108 is in a neutral position (FIG. 3) and when a known amount of torque is applied to the knee joint 108 while taking the knee through its determined range of motion (FIG. 4). Preoperative data may further include forces acting on the joint or through the joint, such as forces resisting movement, while the patient's joint is being positioned or guided through a range of motion.

Figure 5:
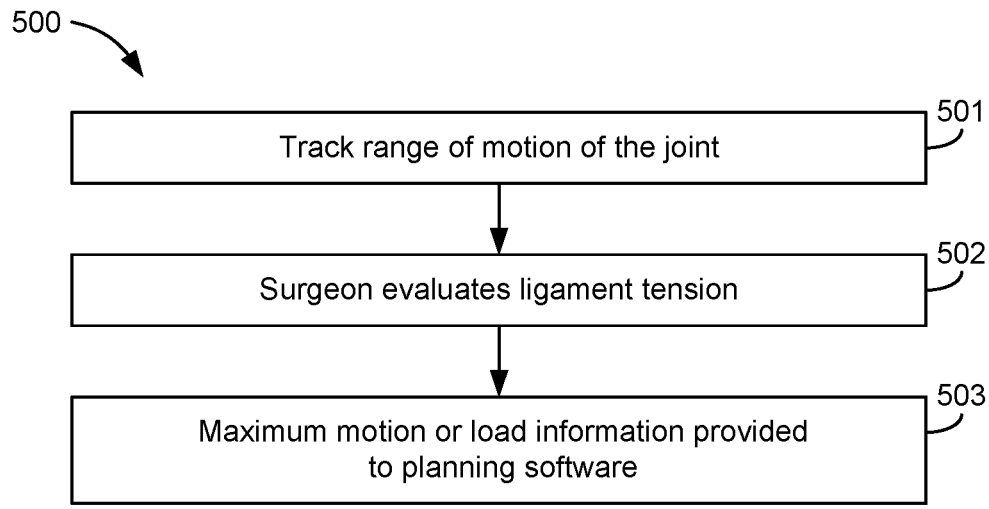
FIG. 5 is a flow chart of a preoperative process for determining the load and displacement limits for a joint, according to an exemplary embodiment.
Figure 6:
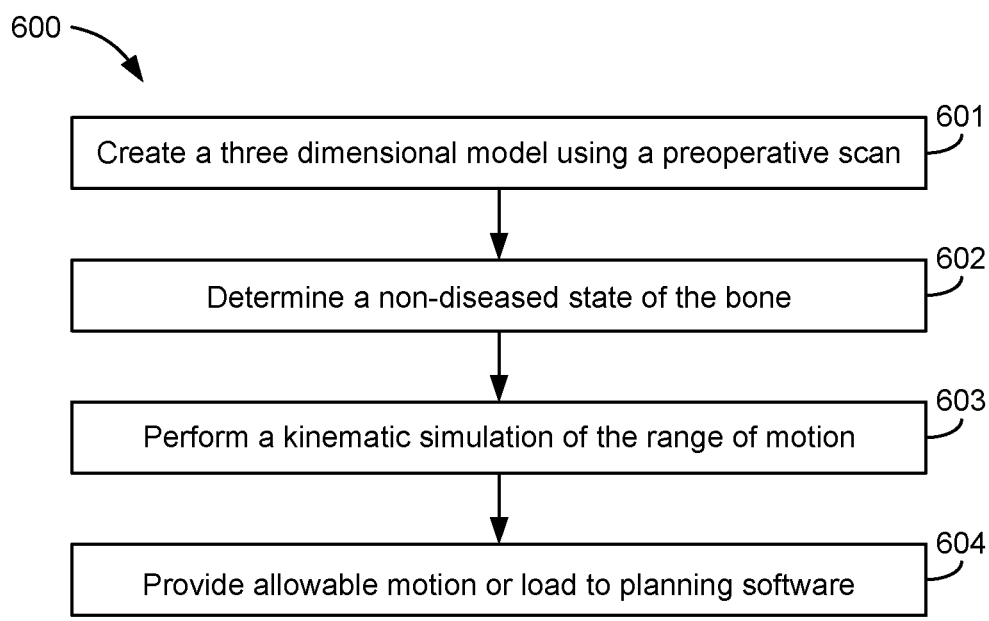
FIG. 6 is a flow chart of another preoperative process for determining the load and displacement limits for a joint, according to an exemplary embodiment.
Figure 7:
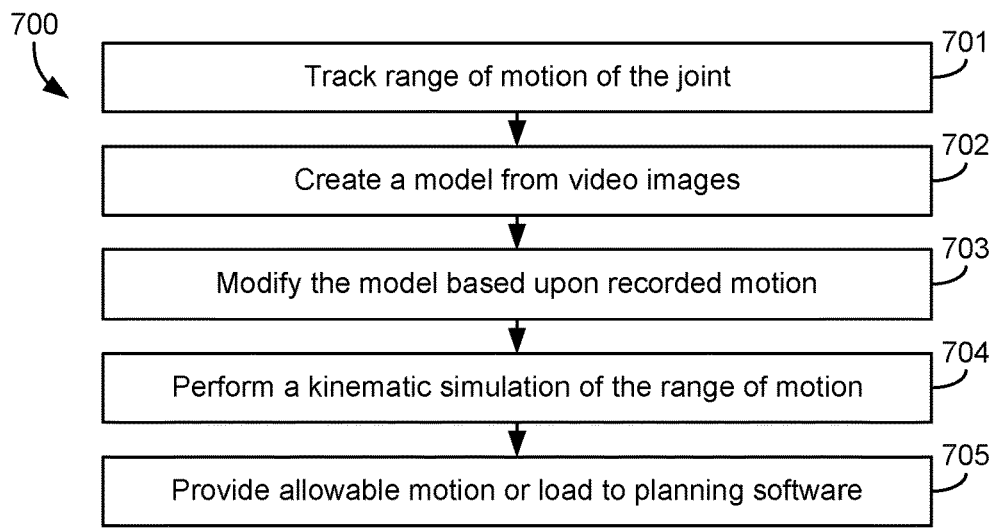
FIG. 7 is a flow chart of another preoperative process for determining the load and displacement limits for a joint, according to an exemplary embodiment.

Pre-operatively analyzing the joint load and displacement maximums is not required before a robotically-assisted ligament balancing procedure, and in such cases, limits may be defined within the CAS system 200 in another manner. FIGS. 5-7 depict three embodiments of this optional preoperative procedure for defining the load and/or displacement limits of the joint. In each of the embodiments, a tracking system, such as any of the tracking systems described above, is used to track the anatomy of the patient while the joint is being moved through the range of motion. In some embodiments, the tracking may take place in the physician's office or a therapy room. In other embodiments, the tracking takes place in the operating room just before the procedure. The range of motion actions could be predefined motions such as flexion-extension or drawer pull motions, or could be surgeon defined motions entered into the CAS system.

FIG. 5 depicts a first exemplary process 500 for determining the load and displacement limits for a joint. In step 501, the range of motion is tracked by tracking the position of the bones (i.e. the femur and the tibia) as the joint is moved through the range of motion. The surgeon or medical provider may apply a passive pressure to move the joint through a natural range of motion, or a stress could be applied to evaluate a stress-induced motion. The surgeon may use a load measuring device to measure the pressure applied to the patient while moving the joint through a range of motion. The measurements from the range of motion manipulation are evaluated by the surgeon or medical provider in step 502. Specifically, the range of motion parameters are determined based upon measurements made during the test. These values can indicate the angle of motion for a variety of tests or directions of pulling to evaluate ligament laxity. In step 503, the limits determined from the evaluation in step 502 may be manually entered by the surgeon or medical provider into the CAS system 100 to be used during the ligament balancing procedure, or the values may be automatically loaded into the planning software from the tracking system.

FIG. 6 depicts a second exemplary process 600 for determining the load and displacement limits for a joint. In step 601, a preoperative scan is used to create a three-dimensional model of the joint, or several two-dimensional models. Process 600 may continue with optional step 602 during which a reverse disease progression model is used to determine the non-diseased state of the bone(s) of the joint. In some embodiments, the non-diseased state of the cartilage and the bone can be determined using the method described in International Publication Number WO 2017/085478, entitled "Image Processing Method" which is incorporated by reference herein in its entirety. In step 603, the preoperative scan three-dimensional model (from step 601) or the non-diseased bone model (if available from step 602), is used to perform a kinematic simulation of the range of motion of the joint. Alternatively, in embodiments where neither the preoperative scan three-dimensional model nor the non-diseased bone model is available, a bone model may be created instead from the kinematic motion tracked in a step similar to step 501 of process 500. In some such embodiments, a calculation or preset parameters, based on the pre-operative condition of the bones and the recorded motion, are used in place of a kinematic simulation. Data and information from the kinematic simulation or calculations based on recorded motion is imported, in step 604, to the planning and guidance software of CAS system 100, providing the allowable displacements and/or loads for the tissue balancing procedure.

FIG. 7 depicts a third exemplary process 700 for determining the load and displacement limits for a joint. In step 701, similar to step 501, the range of motion is tracked using a tracking system. In this embodiment, video images are used to create a three-dimensional model of the joint (step 702). An initial generic or statistical model could be provided and modified for the specific patient. In step 703, the three-dimensional model is modified based on information related to the tracked motion of the bones of the joint. In step 704, the three-dimensional model is used to perform a kinematic simulation of the range of motion of the joint. Data and information from the kinematic simulation is imported, in step 705, to the planning and guidance software of CAS system 100, providing the allowable displacements and/or loads for the tissue balancing procedure. In some embodiments, the range of motion tracked in step 701 may be used as the allowable motion for step 705, and steps 702, 703, and 704 are not performed. In yet another embodiment, an additional step, similar to step 603 to restore the model to a non-diseased state, may be performed between steps 703 and 704.

The result of processes 500-700 are defined load and/or displacement limits for one or more motions of the joint, which may be used during a robotic ligament balancing analysis.

Figure 8:
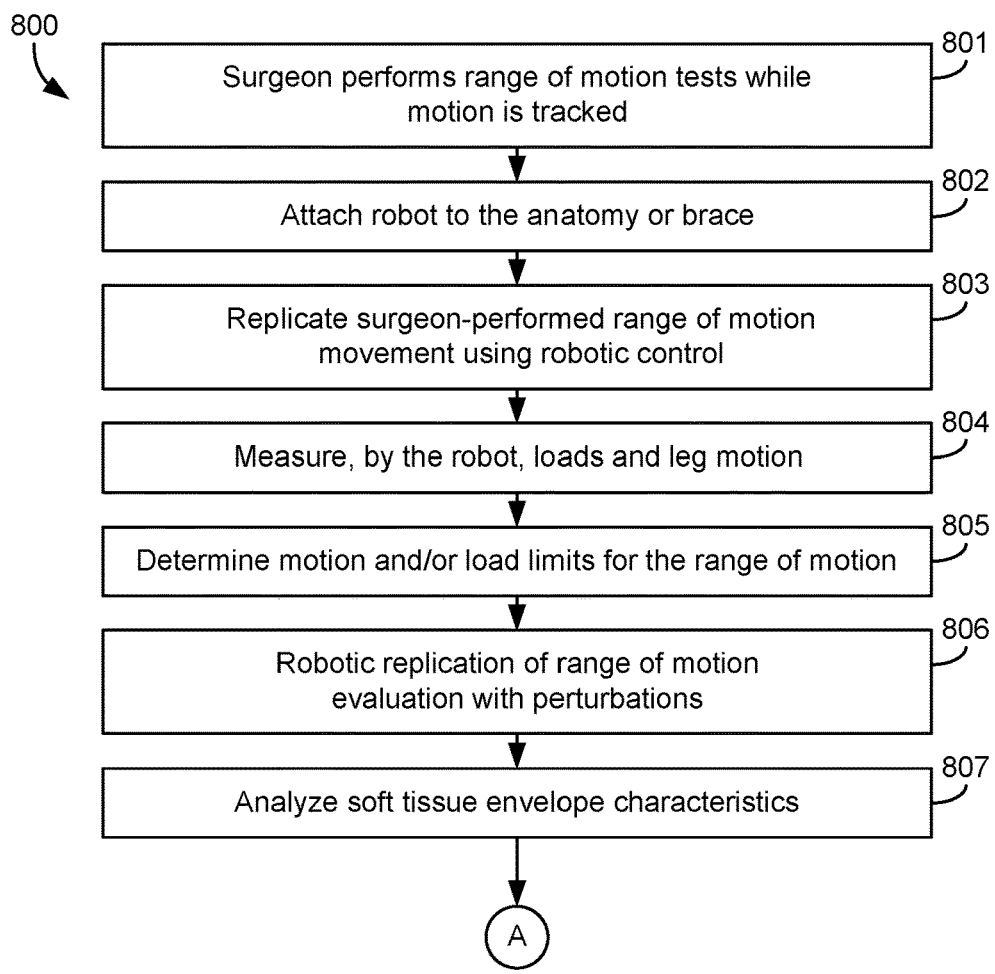
FIG. 8 is a flow chart of an intraoperative process determining the soft tissue characteristics of a joint, according to an exemplary embodiment.
Figure 9:
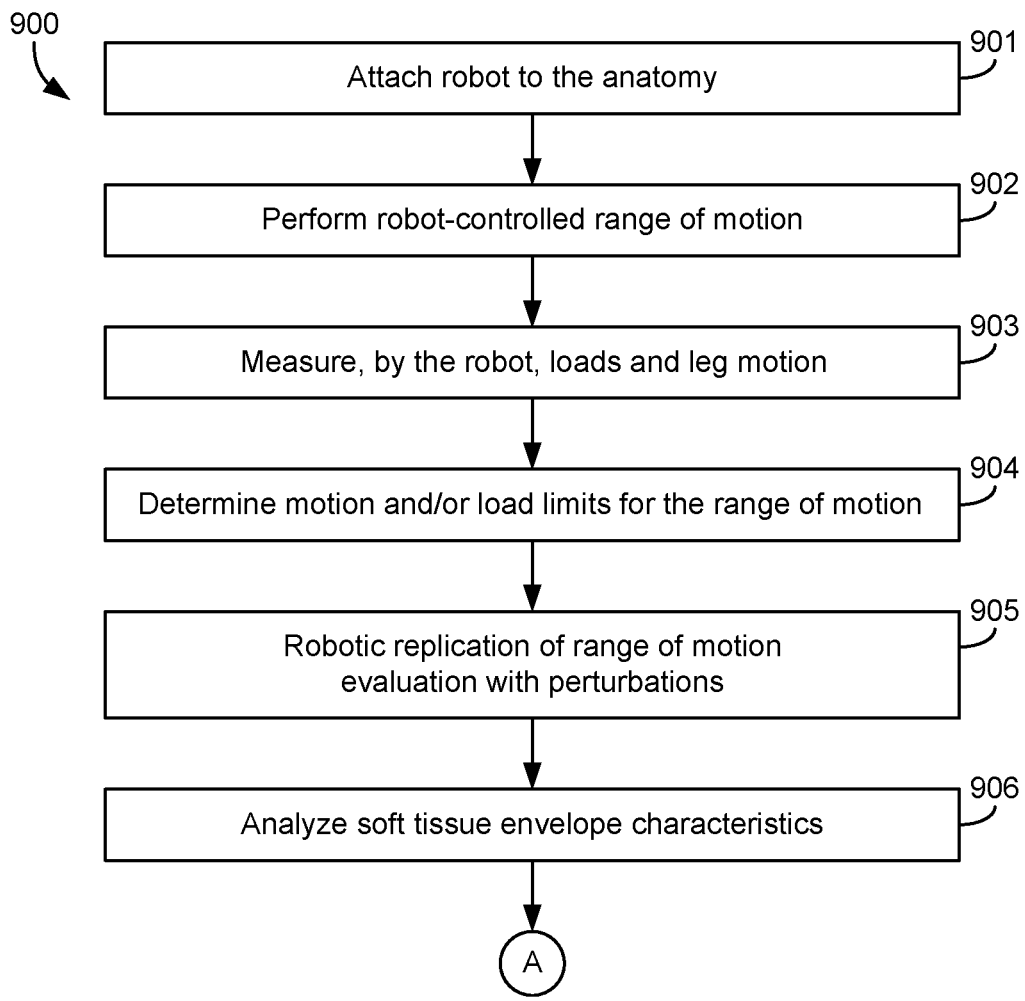
FIG. 9 is a flow chart of another intraoperative process determining the soft tissue characteristics of a joint, according to an exemplary embodiment.
Figure 10:
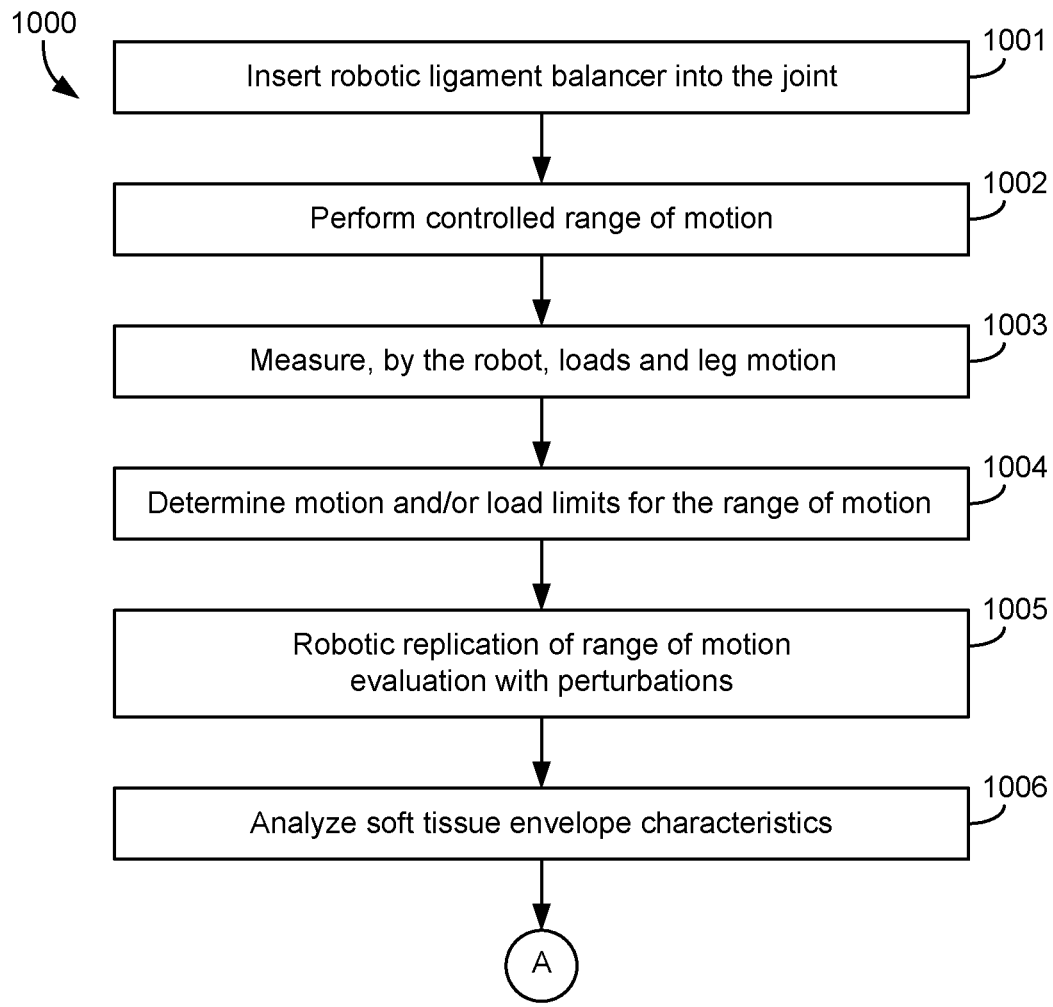
FIG. 10 is a flow chart of another intraoperative process determining the soft tissue characteristics of a joint, according to an exemplary embodiment.

Various exemplary processes 800-1000 for an intraoperative robotic ligament balancing analysis are depicted in FIGS. 8-10. In these processes, the robotic system is used to manipulate the joint and evaluate the soft tissue. During the robotic ligament balancing analysis, the characteristics of the soft tissue are determined, such as characterizing a soft tissue envelope. The processes 800-1000 can be performed with or without having completed the preoperative displacement and load evaluations (processes 500-700) described above. The embodiments shown include steps to define the load and displacement limits of the joint, however, where the preoperative processes 500-700 have been performed, the resultant data may be fed into processes 800-1000 in place of executing some of the early intraoperative steps, as explained below.

FIG. 8 depicts a first exemplary process 800 for determining the soft tissue characteristics of a joint. Process 800, in most cases, is performed without having performed an additional preoperative analysis of the load and displacement limits. However, the allowable motion and/or load limits determined in processes 500, 600, and 700 may be used to define additional safety limitations to any of the process 800, 900, and 1000 described below. In some embodiments, process 800 includes use of a manual spacer positioned in the joint. In process 800, the surgeon manually manipulates the joint and the robotic ligament evaluator system 200 recreates the tracked movement. More particularly, in step 801, the surgeon manipulates the joint through the range of motion while stressing the joint to the limits acceptable for the patient, based on the surgeon's subjective observation of the behavior of the joint. The motion of the bones of the joint are tracked, in a similar fashion as described above with respect to processes 500, 600, and 700.

Next, in step 802, the robotic device 202 is attached to the mobile (e.g., distal) bone(s), to the soft tissue, or to the thigh brace 208 or foot brace 210. Again, specifically referencing the knee joint 108, the thigh brace 208 and the foot brace 210 are coupled to the patient's thigh and foot, respectively, to control movement of the femur and tibia, respectively. Similarly, the clamp 228 is coupled to the thigh brace 208, if not already coupled, and fastened to a surface (e.g., the operating table 102) to keep the thigh brace 208 stationary. The robotic arm 204 of the robotic device 202 is then coupled to the foot brace 210 by the interface tool 212 of the robotic arm 204 and the robotic arm interface 230 of the foot brace 210. In some embodiments, the femur is not held stationary, and instead, both the femur and the tibia are controlled by the robotic device 202.

In optional step 803, the robotic ligament evaluator system 200 then replicates the range-of-motion evaluation performed by the surgeon in step 801. In step 804, the robotic ligament evaluator system 200 measures information about the joint, such as the loads that were applied to the joint, during the range-of-motion evaluation. This range-of-motion evaluation may be either the tracked range of motion evaluation of step 801, or the replicated range of motion performed by the robotic device 202 during step 803, if performed. In one embodiment of step 804, the CAS system 100 may determine and calibrate the forces through an open-loop force generator. For example, the CAS system 100 may monitor a robot current torque applied to a robotic joint, as well as the motor current resistance provided by the robotic joint, and increase the torque applied to the robotic joint until the resistance provided by the joint reaches a certain level. In another embodiment of step 804, the CAS system 100 may instead determine and calibrate the forces through a force-torque sensor (e.g., included in the robotic ligament evaluator system 200). For example, a force-torque sensor provided on the evaluator system 200 may measure the amount of force and torque applied to guide the joint through each point of the spatial trajectory of the initial ROM.

From the information and measurements of step 804, the CAS system 100 determines, in step 805, the load or displacement limits of the joint for the range of motion. For example, the amount of force or torque that can safely be applied to the joint while articulating the joint (e.g., the amount of force that can be applied to the joint without injuring the joint) based on the movement during the surgeon's articulation of the joint and/or the amount of force or torque used by the surgeon in articulating the joint, and thereby creates a baseline reference load for the joint. In other words, during intraoperative steps 801-804, the motion and displacement limits of the joint are determined intraoperatively, in a similar fashion as preoperative processes 500-700. If the limits of the joint have been determined by, for example, the processes 500-700, such limits can be provided to the CAS system, and process 800 for characterizing the soft tissue envelope begins at step 805 using the resultant data of the preoperative process 500-700. In other embodiments, the process 800 may begin at step 805 with the limits manually entered by the surgeon or using date from any other process for determining the load or displacement limits of the joint.

Again, defining these limits is important when tissue balancing is being performed by a robotic system rather than by a surgeon who can "feel" the range of motion and the limits to a patient's range of motion. Indeed, the forces/torques needed to guide the joint of one patient through its range of motion may be different from the forces/torques needed to guide the joint of another patient. Similarly, the forces/torques withstood by the joint of one patient may be different from the forces/torques withstood by the joint of another patient. Additionally, the determined amount of force or torque may vary based on the direction and/or type of articulation provided while guiding the joint through its range of motion. For example, the CAS system 100 may determine, as the evaluator system 200 is articulating the joint, that the surgeon applied five pounds of force in the medial direction but ten pounds of force in the lateral direction. In doing so, the CAS system 100 may obtain reference criteria for balancing the joint based on the recreation of what the surgeon did at step 801. The result of this process may be a range of forces and torques that the CAS system 100 determines may be safely applied to the joint (e.g., a range of forces and torques that may be used to successfully guide the joint through its range of motion without stressing or injuring the joint). If the load in one direction of articulation is higher than the other, then the lower load may be set as the maximum load for that particular test. Different maximum loads can be defined for various ligament tests (push/pull drawer, varus/valgus flexed, varus/valgus extended, joint rotations, etc.). Accordingly, step 805 is training the robotic system on a range of motion that is appropriate for one or more tests of the particular patient. From step 805, the robotic system understands the displacement and load limits for the range of motion of the patient, which will be utilized as the process proceeds.

Subsequently, in step 806, the robotic ligament evaluator system 200, or more particularly, the joint positioner controlled by the robotic device, which now understands its limits from step 805, replicates the range-of-motion evaluation while introducing perturbations into the range-of-motion spatial trajectories. The perturbations may be performed in a single mode (e.g., only one type of perturbation is performed) or multimodal (e.g., more than one type of perturbation is performed). Different modes of perturbations include providing spatial perturbations or "displacement control" (e.g., flexing or extending the joint), and "load control," such as force perturbations (e.g., moving the joint side-to-side) and torque perturbations (e.g., twisting the joint). Additionally, perturbations may be perpendicular and/or tangential to the momentary axis of rotation of the joint. In step 806, the perturbations provided by the robotic ligament evaluator system 200 replicate actions that are normally performed manually by the surgeon, but are now being carried out by the robot. Since the manual manipulation is replaced by the robotic manipulation, the robotic ligament evaluator system 200 uses its "training" and implements force control based on the previously determined load and/or displacement limits of the joint during the range of motion replication, i.e., uses the zero baseline references forces determined in step 805 to ensure that the system 200 does not apply too much or too little force to the knee joint 108. Throughout this process, the CAS system 100 gathers data on the joint as it is guided through the perturbations (e.g., data on the gap in the joint, data on the resistance offered by the joint, etc.).

Referencing the knee joint 108, the robotic haptic device 202 replicates the initial ROM while adding in additional perturbations to the spatial trajectories of the recorded initial ROM. For example, as the robotic haptic device 202 guides the knee joint 108 through the initial ROM, the robotic haptic device 202 may flex and extend the knee joint 108, move the knee joint 108 laterally from side-to-side, and/or twist the knee joint 108. Furthermore, the robotic haptic device 202 may include perturbations designed to test the function of the patient's anterior cruciate ligament (ACL) and/or posterior cruciate ligament (PCL). The perturbation may further be specific to a type of issue manifested in the joint. For instance, the flexion-extension perturbations performed for a knee joint 108 with a varus deformity (i.e., the knee joint 108 causes the tibia 106 to angle inward) may be different from the flexion-extension perturbations performed for a knee joint 108 with a valgus deformity (i.e., the knee joint 108 causes the tibia 106 to angle outward).

The CAS system 100 then, in step 807, uses the data from the perturbations to characterize the constraints of the soft tissue envelope surrounding the joint. In doing so, the CAS system 100 characterizes the soft tissue envelope constraints in an objective and quantifiable manner, an advancement over manual tissue balancing. In one embodiment, the CAS system 100 characterizes the constraints as a force-displacement relationship across the joint's range of motion. In another embodiment, the CAS system 100 characterizes the constraints using a spring-damper representation of the soft tissue envelope. For example, with reference to the knee joint 108, the CAS system 100 may use the data from the perturbations performed at step 806 to characterize the soft tissue (e.g., the ligaments, the tendons, the fibrous tissues, etc.) surrounding the knee joint 108 in a force-displacement relationship across the knee joint's 108 range of motion or as a spring-damper relationship. The soft tissue envelope can be displayed and characterized to update the surgical plan.

FIG. 9 depicts a second exemplary process 900 for determining the soft tissue characteristics of a joint. Process 900 is similar to process 800 except that process 900 does not include manual articulation of the joint as in step 801. Instead, process 900 begins with attaching the robotic device 202 to the thigh and foot of the patient (step 901) to robotically control the tibia and/or the femur. In step 902, a robot-controlled range of motion is performed. The load and/or displacement limits for the range of motion tests can be defined intraoperatively during steps 903-904 of process 900 in a similar fashion as steps 804-805 of process 800, or by carrying out any of the preoperative processes 500-700 described above, or by executing any joint motion. For example, the surgeon could define any motion to use for balancing and can have the system carry out the motion by providing an input to the CAS system 100. In either case, the load and displacement limits of the joint are provided to the robotic system at step 904, and steps 905-906 of process 900 are carried out in the same or similar fashion as steps 806-807 of process 800.

In some embodiments of process 900, such as where preoperative processes 500-700 are performed to determine the limits of the joint, the full range of motion is not performed by the robotic device 202, and instead, after attaching the robotic device in step 901, the process moves directly to step 905 where small perturbations are applied to the joint by the robot. The process continues with step 906 as described above. In some embodiments, process 900 includes use of a manual spacer positioned in the joint.

In the foregoing processes 800 and 900, the initially captured ROM also provides the baseline for the physiological kinematic envelope of the joint. Not only is the position of one bone relative to the other across its natural displacement envelope (e.g. tibia motion as a function of flexion relative to the femur) acquired, but also the static loads at any given configuration (e.g. forces and moments required to hold the tibia at any particular position relative to the femur). In an active situation where the patient performs the motion, the related dynamic information can also be captured using methods well-established in the art using motion capturing solutions and force sensors to capture ground reaction forces as well as electromyography to synchronize muscle activity, motion and forces.

The acquisition of the above information is useful for performing the soft tissue evaluation according to the present disclosure. Tibia motion relative to the femur as a function of flexion represents a safe envelope for the joint, which can be used as input for automated manipulations by the robot and more specifically as a safety boundary for robot enabled manipulations. Static loads can be used, as described further above, not only to enable a weightless manipulation of the mobile entity by compensation forces and torques required to suspend the entity at a given position, but also as a zero baseline to establish an initial reference ligament forces state. A perturbation of this initial state can be useful to determine the ligament envelope characteristics at any given position within the motion envelope. Dynamic information can be used in combination with relative bone motion and static loads to precisely impart the tension as forces and torques to the ligament envelope of the joint as experienced in active motion.

FIG. 10 depicts a third exemplary process 1000 for determining the soft tissue characteristics of a joint. Process 1000 is similar to process 900 except that in step 1001 a device to tension the ligaments is positioned in the joint. The device could be a spacer, a trial implant, forceps, or other device. In the embodiment shown in FIG. 10, the device is a robotic ligament balancer inserted into the joint instead of or in addition to attaching the robotic device to the foot and thigh of the patient (as in step 901). The robotic ligament balancer is controlled by the robotic device to distract the joint. In some embodiments, the device measures the loads applied in the joint. In some embodiments, robotic control of the tibia and/or the femur is also used. In step 1002, a controlled range of motion is performed. The range of motion may be controlled by the robotic system or by the surgeon. The load and/or displacement limits for the range of motion tests can be defined intraoperatively during steps 1003-1004 of process 1000 in a similar fashion as steps 804-805 of process 800, or by carrying out any of the preoperative processes 500-700 described above, or by input from the surgeon. In any of these case, the load and displacement limits of the joint are provided to the robotic system at step 1004, and steps 1005-1006 of process 1000 are carried out in the same or similar fashion as steps 806-807 of process 800.

The soft tissue envelope characteristics along the joint's range of motion, determined by processes 800-1000, are analyzed to optimize the surgical strategy. The result of the surgical strategy should be a balanced, stable joint. This analysis may be done manually by a surgeon, by the CAS system 100, or by a surgeon working in concert with the CAS system 100. In some embodiments, the surgical strategy includes the placement of prosthetic components to achieve a certain soft tissue characteristic pattern across the joint's range of motion. For example, the surgical strategy may include a prosthetic placement optimized to achieve a certain joint space or certain ligament loads. A prosthetic placement (such as by an automated planning algorithm) may be programmed into the planning software to automatically position the prosthetic component based on the defined soft tissue envelope. In other embodiments, the surgical strategy includes determining a preferred distance between two bones of the joint and/or defining a preferred alignment between two bones of the joint. In further embodiments, alternatively or additionally, the surgical strategy may include the manipulation of tissue (e.g., dissection of ligaments, tightening of ligaments, removal of osteophytes, etc.) to achieve a certain kinematic characteristic across the joint's range of motion. For example, the surgical strategy may include tissue manipulation to achieve a certain spatial position of the joint line across the range of motion relative to the position of the joint bones.

Referring specifically again to the knee joint 108, in one embodiment, the surgical strategy based off of the soft tissue envelope characterized at Steps 807, 906, and/or 1006 may include the placement of one or more knee replacement prosthetics optimized to achieve a certain space in the knee joint 108 and/or certain loads of the ACL or PCL. In another embodiment, the surgical strategy may include dissecting, and thereby lengthening, of tight ligaments in the knee joint 108 to achieve a certain spatial position of the knee joint 108 line across the range of motion of the knee joint 108. In a third embodiment, the surgical strategy may include both the placement of one or more knee prosthetics in the knee joint 108 and manipulation of the soft tissue surrounding the knee joint 108.

Figure 11:
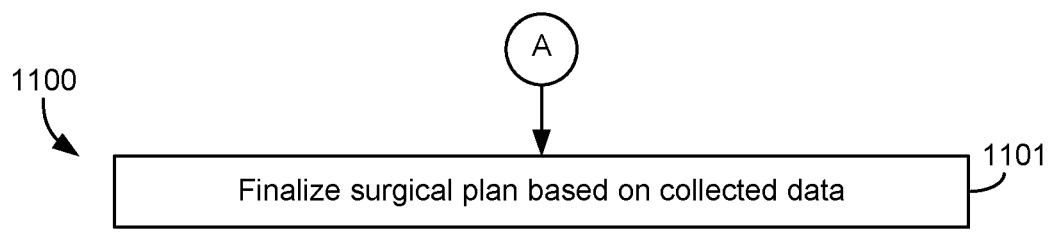
FIG. 11 is a flow chart of an intraoperative surgical planning process for optimizing a surgical strategy using the soft tissue envelope characteristics, according to an exemplary embodiment.

FIGS. 11-15 depict various exemplary processes for intraoperative surgical planning for optimizing a surgical strategy using the soft tissue envelope characteristics. In FIG. 11, process 1100 finalizes the surgical strategy (step 1101) based on the data collected in the soft tissue analysis of processes 800-1000. In this embodiment, the surgical strategy may include a prosthetic placement optimized to achieve a certain joint space or certain ligament loads. This process may not require any tissue manipulation in order to achieve the desired balance, and instead, can be achieved by a specific prosthetic placement, determined based on the data of the joint obtained during the intraoperative analysis.

Figure 12:
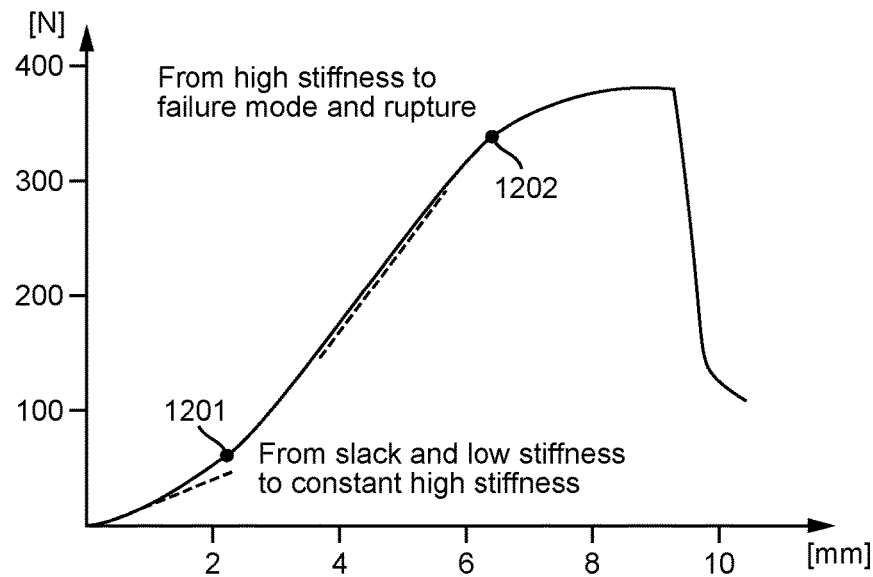
FIG. 12 depicts a force-displacement curve of a joint used to determine stiffness transition points for the joint.

Soft tissue envelope characteristics across the range of motion of a joint may be determined as a function of the first transition point of the ligament stiffness. While the following discussion of the stiffness transition points refers specifically to the knee joint and to the tibia and femur, it is understood that the same or similar concepts are applicable to evaluation of soft tissue of any joint. FIG. 12 shows a typical force displacement curve of a ligament of a knee joint, as an example. The curve depicts four characteristic behaviors of the ligaments as they are stretched. The first zone depicts the transition from slackness to high stiffness before the first transition point 1201, where all fibers of the ligament are engaged in stress sharing. A second zone, between the first transition point 1201 and the second transition point 1202, shows a linear behavior of ligament stiffness over a wide range of force until transitioning (at the second transition point 1202) into a third zone where fibers begin to fail, therefore diminishing its stiffness. This is followed by its rupture and complete failure depicted in the fourth zone at the end of the curve.

The region between the two stiffness transition points 1201, 1202 is a region of high, linear ligament stiffness. Typical soft tissue assessments methods employ an arbitrary load in this segment to assess soft tissue stability. One of the many challenges to objectively characterize the soft tissue stiffness in the knee joint is that it is patient dependent and changes across the range of motion of the knee and is heavily biased if the patella is not in place or more so, if it is everted. Utilizing a fixed arbitrary load may yield a response in either of the two initial stiffness segments. Failing to discern their relationship may result in improper soft tissue balance yielding a too loose configuration which will present itself as instability or a too tight configuration which could manifest itself as pain.

By establishing the first stiffness transition point 1201 of the soft tissue envelope of the knee across its entire range of motion (or parts of it), proper tension of the arthroplastic construct can be achieved by an appropriate spatial arrangement between the tibia and the femur to re-establish the previously determined stiffness transition points.

The robot enabled perturbation motion described herein can be used to automatically establish the first stiffness transition point of the soft tissue envelope across its entire range of motion. The result of this operation is the position of the tibia relative to the femur across the entire range of motion of the knee. This information can be used to optimize the positions of prosthetic components with respect to the joint line of the knee, or alternatively to manipulate the soft tissue envelope characteristics to influence the established spatial relationship of the tibia relative to the femur or a combination of both.

Figure 13:
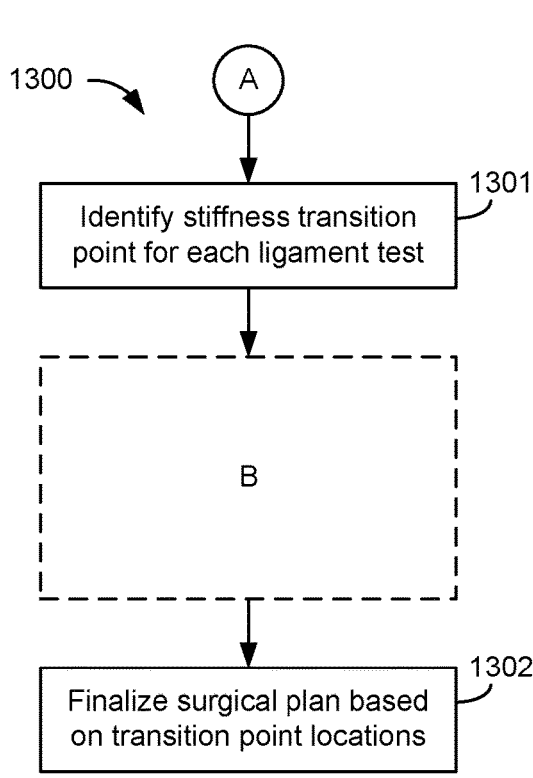
FIG. 13 is a flow chart of another intraoperative surgical planning process for optimizing a surgical strategy using the soft tissue envelope characteristics, according to an exemplary embodiment.
Figure 14:
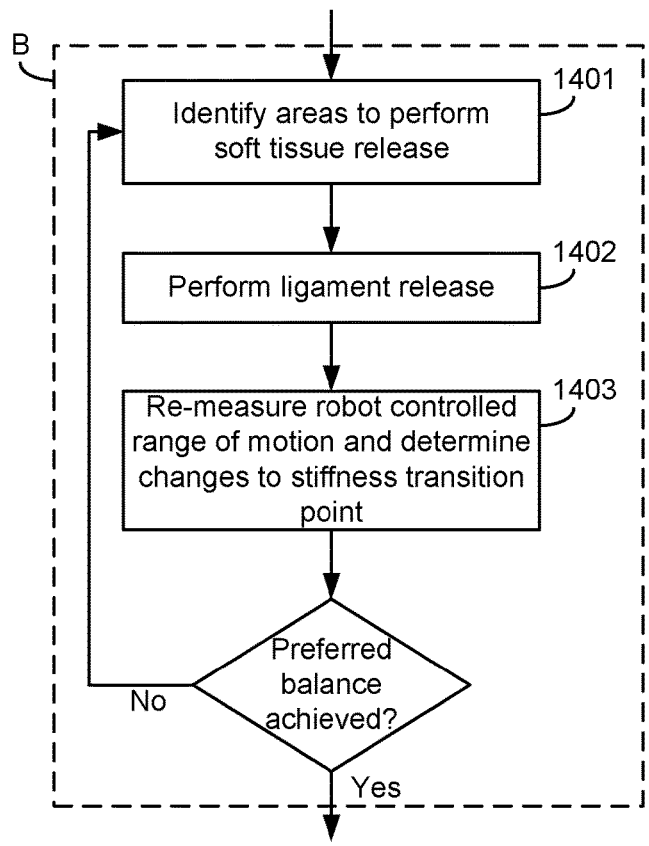
FIG. 14 is a flow chart of an optional sub-process of the process of FIG. 13, according to an exemplary embodiment.

FIG. 13 depicts an exemplary process 1300 for optimizing the surgical strategy utilizing stiffness transition points. During each ligament test evaluation, a stiffness transition point can be identified (step 1301). The surgical plan is finalized (step 1302) based on the point of this change from low to high stiffness. For example, the surgeon can define the desired implant placement based upon the ligament balance information collected utilizing the stiffness transition point. Process 1300 also includes optional process B, which is depicted in FIG. 14. Once identified, it is determined whether the stiffness transition point occurs at the expected/desired point during the range of motion movement. If the stiffness transition point is not as expected or desired, tissue manipulation, such as tissue releases, may be performed to achieve the desired stiffness transition point(s) of the ligaments (and hence, the proper joint balance). More particularly, in step 1401, areas for performing a tissue release are identified based on the stiffness transition point(s) of the ligament(s). In step 1402, the ligament is manually released. In step 1403, the robot-controlled range of motion is repeated to determine the stiffness transition point now that the ligament release has occurred. If the preferred balance is not achieved, the process returns to step 1401 and repeats until the preferred balance is achieved. Once achieved, the surgical plan is finalized (step 1302).

Figure 15:
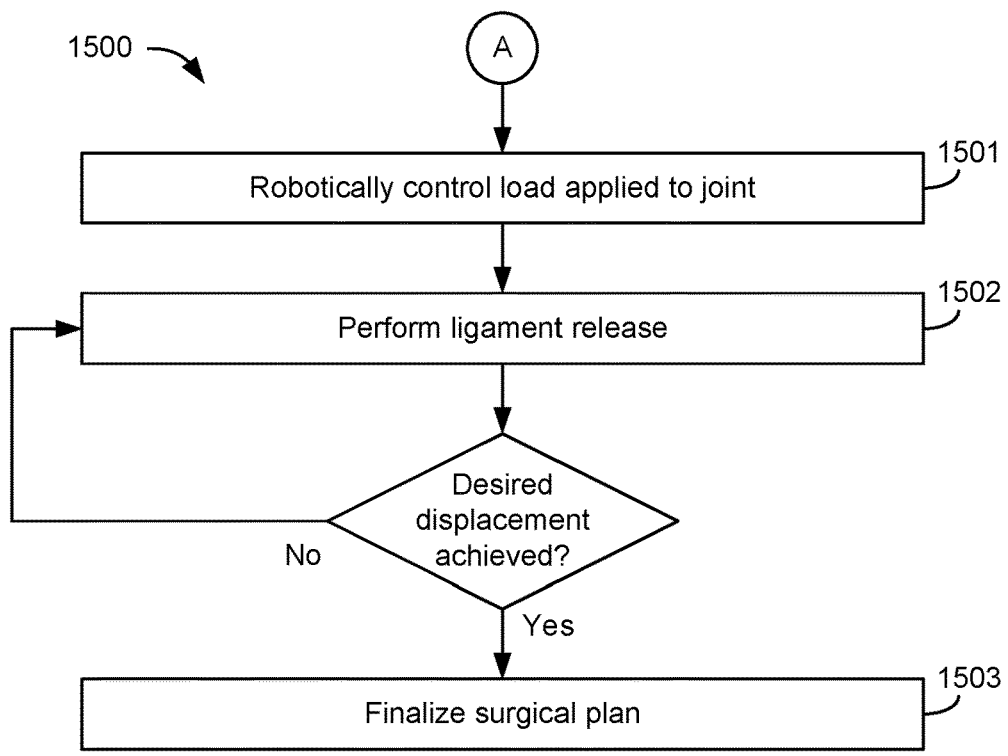
FIG. 15 is a flow chart of another intraoperative surgical planning process for optimizing a surgical strategy using the soft tissue envelope characteristics, according to an exemplary embodiment.
Figure 16:
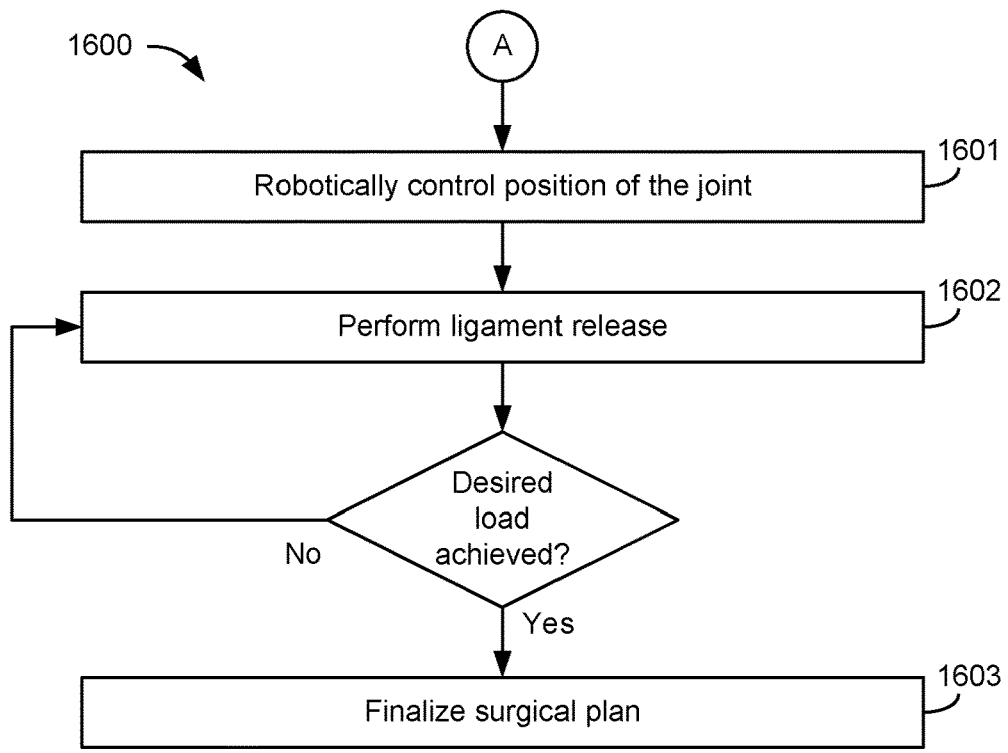
FIG. 16 is a flow chart of another intraoperative surgical planning process for optimizing a surgical strategy using the soft tissue envelope characteristics, according to an exemplary embodiment.

FIGS. 15 and 16 depict additional exemplary processes 1500 and 1600 that incorporate tissue manipulation for optimizing a surgical plan. Processes 1500 and 1600 can be used in place of the manual tissue release of step 1402, and step 1402 is therefore performed using a robotically assisted tissue release as described in process 1500 and 1600. In step 1501 of process 1500 the robotic device 202 applies a controlled load to the joint and the surgeon completes ligament release(s) (step 1502) until the desired displacement is achieved. Once the desired displacement is achieved, the surgical plan is finalized (step 1503). Alternatively, in step 1601 of process 1600 the robotic device 202 applies a controlled displacement to the joint and the surgeon completes ligament release(s) (step 1602) until the desired load is achieved. Once the desired load is achieved, the surgical plan is finalized (step 1603). In either process, the range of motion test may be repeated to confirm proper balancing prior to finalizing the surgical plan.

There are several benefits to using the methods presented in FIGS. 5-11 and 13-16 for performing a ligament tension evaluation, as described above. As noted, traditionally this evaluation has been performed manually by surgeons. By performing this evaluation with the CAS system 100, some of the subjective judgment inherent with the surgeon manually performing a ligament tension evaluation is removed. Additionally, the CAS system 100 allows for the surgeon to make digital pre-operative plans before beginning a surgical procedure, which may increase the likelihood that the procedure will be successful and not result in complications. Furthermore, the methods takes into account variations between the forces and torques that may be applied to the joints of different patients (e.g., the range of forces and torques that may be safely be applied to a joint of a large, young man as opposed to the range of forces and torques that may safely be applied to a small, older woman).

Using the CAS system 100 also allows for improvements to future procedure planning. The post-operative range of motion of the joint can be evaluated (with or without the use of the robotic ligament evaluator system 200). For example, the range of motion of the joint could be monitored during the rehabilitation process to confirm the surgical plan was achieved. Machines that apply motion and/or measure the range of motion during physical therapy could capture data similar to the CAS system. In addition, the pre-operative range of motion evaluation using the tracking system can be repeated post-operative to determine the post-operative range of motion. The outcomes, in combination with the data obtained during the soft tissue evaluations and surgical planning of the initial procedure using the CAS system 100, can be used to make improvements to the planning processes and procedures to improve future outcomes.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention, in particular, any of the steps of the processes described above may be optional, may be completed in a different order, or may be replaced by steps described in other processes.

Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope this disclosure.

Although a specific order of method steps may be described, the order of the steps may differ from what is described. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish any connection steps, processing steps, comparison steps, and decision.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up, or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

Also, it is contemplated that any optional feature of the inventive variations described may be set forth and claimed independently, or in combination with any one or more of the features described herein. Reference to a singular item includes the possibility that there are plural of the same items present. More specifically, as used herein, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only," and the like in connection with the recitation of claim elements, or use of a "negative" limitation.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another, or with the two members or the two members and any additional intermediate members being attached to one another. Such joining may be permanent in nature or may be removable or releasable in nature.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:

1. A method of evaluating soft tissue of a joint, the method comprising:
  measuring, by a robotic device, information about the joint during a controlled range of motion manipulation of the joint;
  determining a motion limit of the joint using the information about the joint measured during the controlled range of motion manipulation of the joint, wherein the motion limit is at least one of a displacement limit or a force limit of the joint;
  replicating, by a joint positioner controlled by the robotic device and using the motion limit as an input, the controlled range of motion manipulation of the joint while introducing perturbations to the joint to provide a replicated range of motion manipulation; and
  using data obtained during the replicated range of motion manipulation with the perturbations to generate a force-displacement curve representative of the joint;

identifying at least one transition point on the force-displacement curve, wherein the at least one transition point represents a transition from slackness to stiffness in the joint; and providing a surgical plan based on the at least one transition point.

2. The method of claim 1, wherein the joint positioner comprises:
a first brace configured for supporting a first portion of patient anatomy comprising a first bone and anatomy associated with the first bone, and
a second brace configured for supporting a second bone and anatomy associated with the second bone.

3. The method of claim 1, wherein the controlled range of motion manipulation is executed by the joint positioner controlled by the robotic device.

4. The method of claim 3, further comprising tracking joint motion during a manual range of motion manipulation, and wherein the controlled range of motion manipulation is a robotically-controlled replication of the manual range of motion manipulation.

5. The method of claim 1, wherein the controlled range of motion manipulation of the joint is performed with a robotic ligament balancer inserted into the joint, and wherein the robotic ligament balancer is controlled by the robotic device.

6. The method of claim 1, wherein measuring the information about the joint comprises:
monitoring a current torque applied to the joint and a current resistance provided by the joint; and
increasing the current torque applied to the joint until the current resistance provided by the joint reaches a predetermined level; and
wherein determining the motion limit of the joint comprises setting the current torque applied at that level as a zero baseline reference load for articulation of the joint in that direction.

7. The method of claim 1, wherein measuring the information about the joint comprises using a force-torque sensor to measure an amount of force and torque applied to guide the joint through the controlled range of motion manipulation.

8. The method of claim 1, wherein the perturbations are at least one of:
spatial perturbations, force perturbations, or torque perturbation.

9. The method of claim 1, further comprising characterizing constraints of the soft tissue envelope in a spring-damper relationship using the data obtained during the replicated range of motion manipulation.

10. The method of claim 1, wherein the steps are performed intra-operatively, and wherein the method further comprises pre-operatively determining load and displacement limits for the joint.

11. The method of claim 1, wherein the surgical plan is a plan for a surgical correction of the joint.

12. The method of claim 1, wherein providing the surgical plan comprises at least one of: determining a placement of a prosthetic component to be implanted in the joint, determining a preferred distance between two bones of the joint, or defining a preferred alignment between two bones of the joint.

13. The method of claim 1, wherein providing the surgical plan further comprises determining a placement of a prosthetic component to be implanted in the joint based on the at least one transition point.

14. The method of claim 1, further comprising performing at least one soft tissue release to move the at least one transition point on the force-displacement curve of the joint to achieve a preferred balance of the joint.

15. The method of claim 1, further comprising performing at least one soft tissue release in the joint, wherein performing the at least one soft tissue release comprises:
controlling, using the robotic device, a load applied to the joint;
determining a relative displacement between a first bone and a second bone of the joint while the load is controlled and the at least one soft tissue release is performed;
determining that the at least one soft tissue release is complete once the relative displacement achieves a desired displacement.

16. The method of claim 1, further comprising performing at least one soft tissue release in the joint, wherein performing the at least one soft tissue release comprises:
controlling, using the robotic device, a load applied to the joint;
determining a load experienced by the joint while the load is controlled and the at least one soft tissue release is performed;
determining that the at least one soft tissue release is complete once the load achieves a desired load.

17. A surgical system comprising:
a robotic ligament evaluator system comprising a robotic device and a joint positioner comprising:
a first brace configured for supporting a first portion of patient anatomy comprising a first bone and anatomy associated with the first bone, and
a second brace configured for supporting a second bone and anatomy associated with the second bone, and
wherein robotic device is configured to move the joint positioner and measure information about a joint during a controlled range of motion manipulation of the joint, the joint associated with the first bone and the second bone; and
a computer system programmed to:
determine a motion limit of the joint using the information about the joint measured during the controlled range of motion manipulation of the joint wherein the motion limit is at least one of a displacement limit or a force limit of the joint;
control, using the motion limit as an input, the robotic device to move the joint positioner to replicate the controlled range of motion manipulation of the joint while introducing perturbations to the joint to provide a replicated range of motion manipulation; and
use data obtained during the replicated range of motion manipulation with the perturbations to characterize constraints of a soft tissue envelope of the joint.

18. The system of claim 17, wherein:
the robotic device is configured to measure the information about the joint by measuring a current torque applied to the joint and a current resistance provided by the joint;
the robotic device is controllable to increase the current torque applied to the joint until the current resistance provided by the joint reaches a predetermined level; and
the computer system is programmed to determine the motion limit of the joint based on the current torque when the current resistance reaches the predetermined level.

19. The system of claim 17, wherein the robotic ligament evaluator system is configured to operate in at least one of: a first mode where the joint is held in a fixed position, a second mode where the joint positioner actively positions the joint, and a third mode where the joint positioner is passive to allow a user to manually manipulate the joint.

\* \* \* \* \*